United States Patent [19]
Huddart et al.

[11] Patent Number: 6,078,730
[45] Date of Patent: Jun. 20, 2000

[54] HEAT RESPIRATORY CONDUIT

[75] Inventors: Brett J Huddart; Malcolm H Cambridge, both of Auckland, New Zealand

[73] Assignee: Fisher & Paykel Limited, Auckland, New Zealand

[21] Appl. No.: 09/068,707

[22] PCT Filed: Nov. 13, 1996

[86] PCT No.: PCT/NZ96/00127

§ 371 Date: Jul. 6, 1998

§ 102(e) Date: Jul. 6, 1998

[87] PCT Pub. No.: WO97/18001

PCT Pub. Date: May 22, 1997

[30] Foreign Application Priority Data

Nov. 13, 1995 [NZ] New Zealand ............................ 280446
May 2, 1996 [NZ] New Zealand ............................ 286497

[51] Int. Cl.[7] ........................................................ F24H 1/10
[52] U.S. Cl. .......................... 392/480; 392/478; 392/485; 219/536
[58] Field of Search ...................... 392/479–481, 392/485–493; 219/523, 535–6, 538, 544, 549; 128/204.17, 203.26, 203.27

[56] References Cited

U.S. PATENT DOCUMENTS

| | | | |
|---|---|---|---|
| 1,064,190 | 6/1913 | Bill | 392/488 |
| 4,207,457 | 6/1980 | Haglund et al. | 392/488 |
| 4,531,551 | 7/1985 | Eichelberger et al. | |
| 4,768,283 | 9/1988 | Gellert | 29/611 |
| 4,967,744 | 11/1990 | Chua | 128/204.18 |
| 4,993,607 | 2/1991 | Brun et al. | 222/590 |
| 5,357,948 | 10/1994 | Eilentropp | 128/204.17 |
| 5,454,061 | 9/1995 | Carlson | |
| 5,546,930 | 8/1996 | Wikefeldt | 128/201.13 |
| 5,558,084 | 9/1996 | Daniell et al. | 128/203.17 |
| 5,774,627 | 6/1998 | Jackson | 392/497 |

FOREIGN PATENT DOCUMENTS

| | | |
|---|---|---|
| 579384 | 1/1994 | European Pat. Off. |
| 621050 | 10/1994 | European Pat. Off. |
| 0672430A2 | 9/1995 | European Pat. Off. |

*Primary Examiner*—Philip H. Leung
*Assistant Examiner*—Thor Campbell
*Attorney, Agent, or Firm*—Trexler, Bushnell, Giangiorgi & Blackstone, Ltd.

[57] ABSTRACT

This invention is a heated corrugated (21) conduit (7) for use in a respiratory humidification system (5). A heater wire (20) within the conduit reduces the occurrence of condensation or "rain out". The heater wire is spirally wound in a helix or double helix with both ends of the wire available for termination at one end of the conduit.

34 Claims, 8 Drawing Sheets

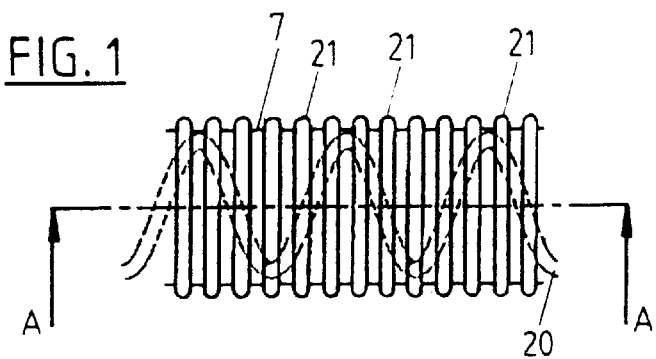
FIG. 1
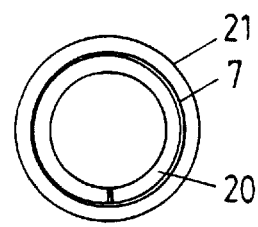
FIG. 2
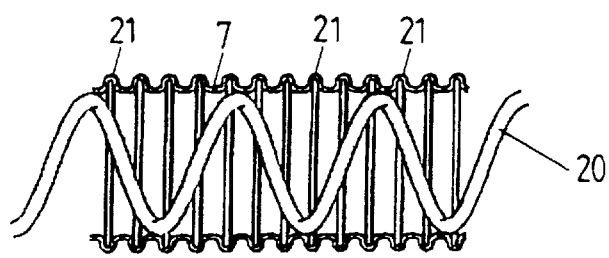
FIG. 3 (Section A-A)
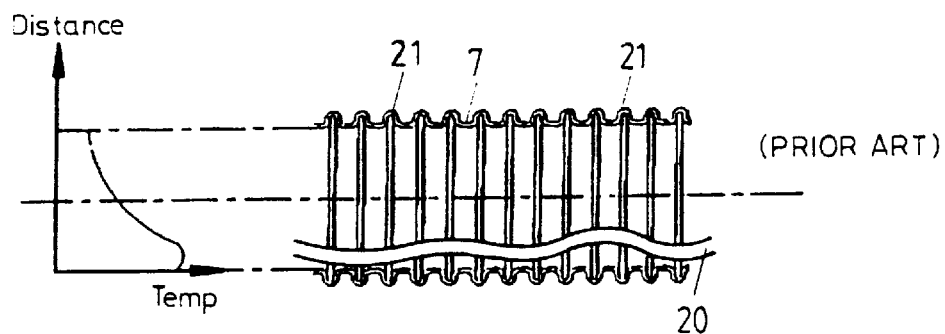
FIG. 5 (PRIOR ART)
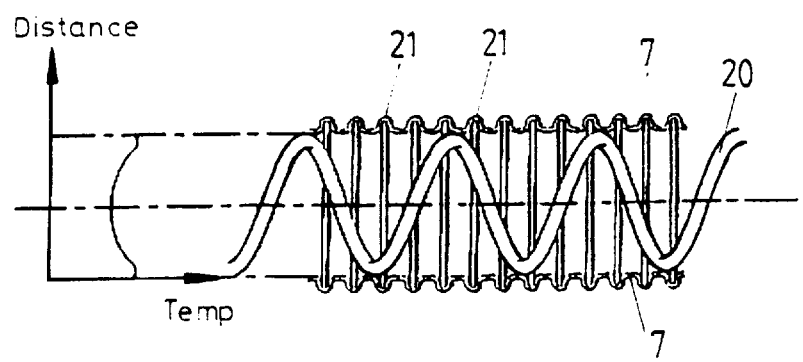
FIG. 6

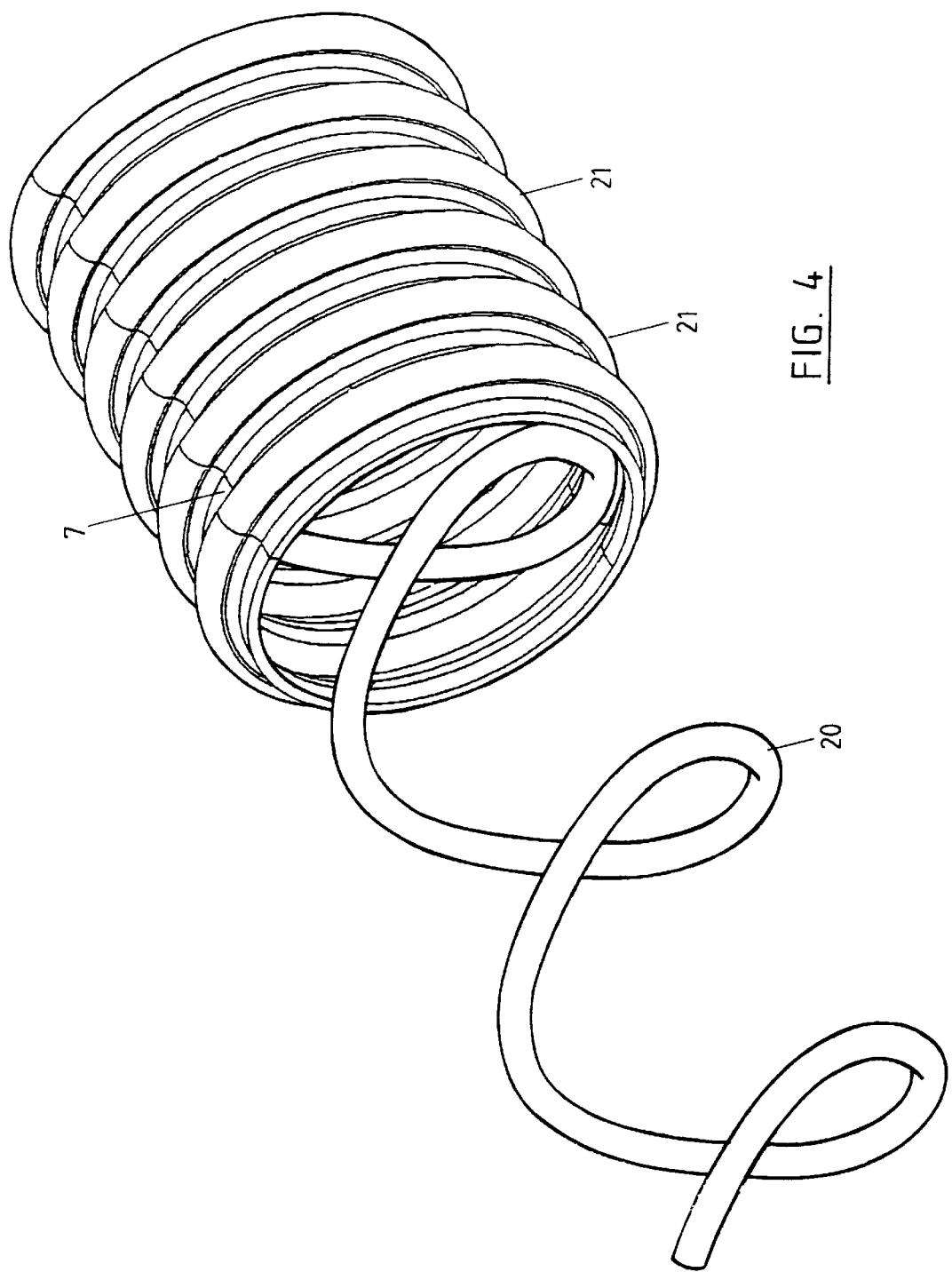

HEAT RESPIRATORY CONDUIT

TECHNICAL FIELD

This invention relates to respiratory humidifiers and more particularly though not solely to heated respiratory humidifier conduits used in the breathing circuits of respiratory humidification systems to provide humidified gases to a patient or other person in need of such gases and methods of constructing such humidifier conduits.

BACKGROUND ART

In order to supply gases, for example humidified gases, to a patient or other person in need of such gases, flexible conduits have been used both from a gases supply to the patient (inspiratory conduit) and from the patient back to the gases supply (expiratory conduit). When the supplied gas is humidified, it is desirable to minimise the amount of condensation (known as "rain out") occurring on the inner walls of the conduit as this condensation soon accumulates, requiring regular draining. Some existing respiratory humidifier conduits incorporate heating wires to heat the conduit walls in an attempt to reduce condensation and also to assist in the control of the temperature of the humidified gases being delivered to the patient.

An example of a respiratory humidifier conduit incorporating a heating wire is disclosed in our prior United Kingdom Patent Application published as GB2284356A on Jun. 7, 1995. The heating wire disclosed is a looped heating element with the two free ends of the loop emerging from one end of the conduit for connection to a source of alternating voltage on the humidifier. This form of heated conduit where the heating wire lies in a random path along the bottom of the conduit has the disadvantage that gases passing through the conduit are not uniformly heated across the width of the conduit. In addition, the random nature of the wire's distribution allows for localised regions of the conduit walls to be at a temperature sufficiently low so as to allow condensation (or "rain out") to occur while other areas are heated excessively.

Some humidifier conduits have a heating wire wound around the outside of the conduit in an attempt to evenly apply heat to the conduit wall (both around the conduit and along the length of the wall) to overcome the problem of condensation. Examples of externally wound heated humidifier conduit may be seen in U.S. Pat. No. 4,686,354 to the BOC Group Plc and German patent publication number DE4244493 to Heinz Eilentropp. Both of these configurations, however, require the power drawn by the heating element to be sufficient to transmit heat through the conduit walls and into the gases. Accordingly, the power drawn by the heater wire is excessive as is the temperature of the wire. In addition, as heat from the heater wire must first pass through the conduit wall, the time taken to heat the gases is excessive, and the temperature of the outer surface of the conduit could possibly be high enough to burn a patient or care giver.

DISCLOSURE OF THE INVENTION

It is, therefore, an object of the present invention to provide a heated gases transportation pathway which goes at least some way towards overcoming the above disadvantages or which will at least provide the industry with a useful choice.

Accordingly, in a first aspect, the invention consists in a heated gases transportation pathway for use in a ventilation system adapted to supply a gases flow within said gases transportation pathway:

a conduit of a predetermined length having an internal surface and a longitudinal axis, a heating means of a predetermined length adapted to heat said gases flow and/or said conduit wherein said heating means is positioned within said conduit means and in said gases flow wherein said heating means are elastically flexible and are formed into a predetermined shape which circumscribes a volume which is a portion of the volume of said conduit.

In a further aspect the invention consists in a heated gases transportation pathway for use in a ventilation system which creates a gases flow comprising:

a conduit adapted to channel said gases flow, a heating means adapted to, upon energisation, supply heat to said gases flow within said conduit, wherein said heating means is provided in said gases flow within said conduit and is preformed such that said gases flow is forced to repeatedly cross said heating means substantially along the full length of said heating means.

In a further aspect, the invention consists in a method of producing a heated gases transportation pathway for use in a ventilation system comprising the steps of:

i) forming a conduit through which gases may be channelled, ii) winding a predetermined length of insulated resistance wire into a helix of a diameter less than the inside diameter of said conduit, and iii) inserting the thus formed helically wound resistance wire into said conduit.

The invention consists in the foregoing and also envisages constructions of which to the following gives examples only.

BRIEF DESCRIPTION OF THE DRAWINGS

FIG. 1 is a front elevation of a section of a heated respiratory humidifier conduit in accordance with the present invention showing hidden detail of the heater wire, FIG. 2 is an end elevation of the conduit shown in FIG. 1, FIG. 3 is a sectional view through the conduit of FIG. 1 along A—A, FIG. 4 is a perspective view of the conduit shown in FIG. 1 showing hidden detail of the heater wire, FIG. 5 is a graph of temperature versus distance across a conventional prior art conduit, FIG. 6 is a graph of temperature versus distance across the conduit shown in FIG. 1.

BEST MODE FOR CARRYING OUT THE INVENTION

Figure 11:
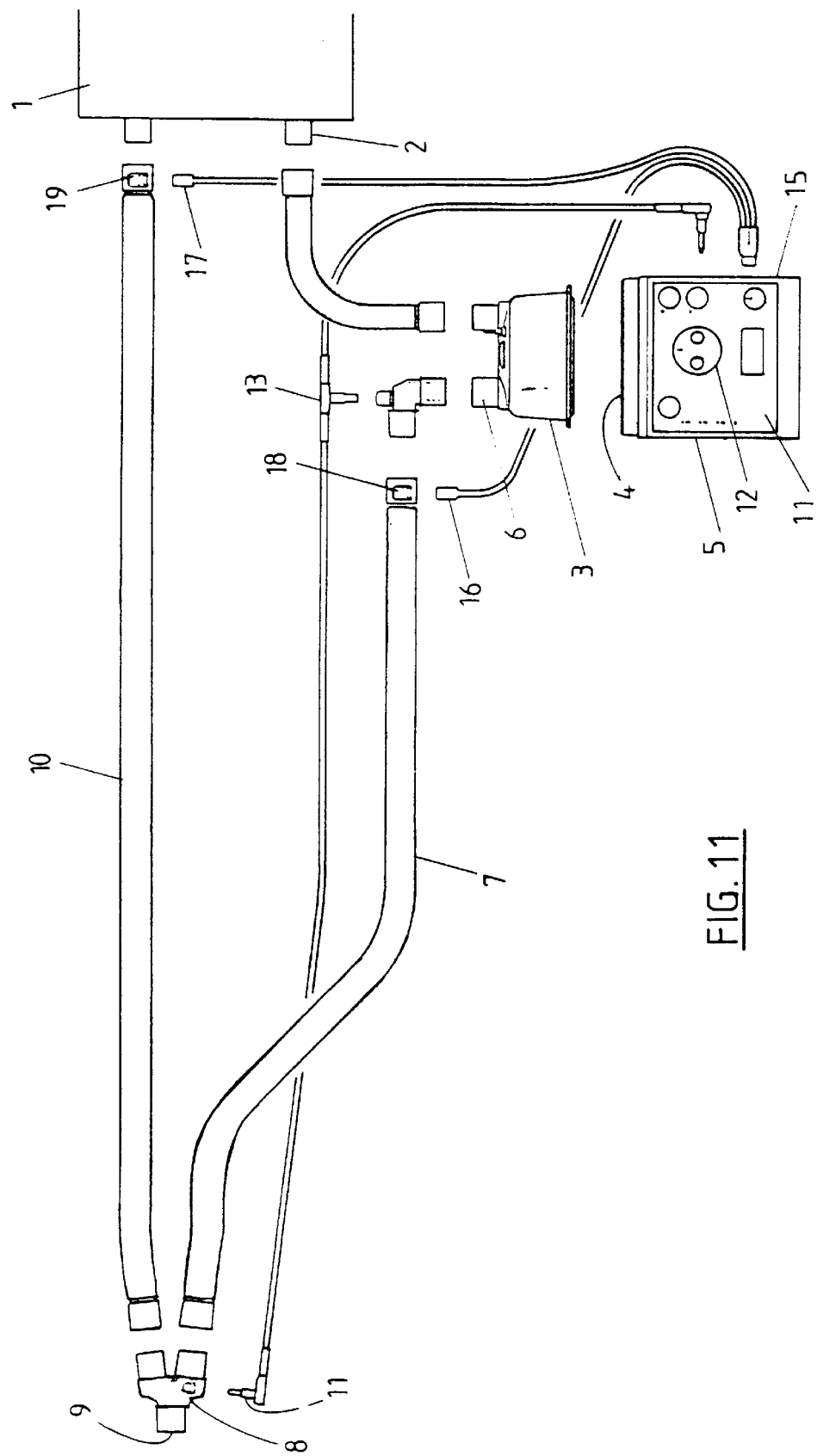
FIG. 11 is an exploded view of a respiratory humidification system including the conduit shown in FIG. 1.

With reference to FIG. 11, a respiratory humidification system is shown wherein a ventilator 1 supplies gases (such as oxygen or anaesthetic gases) through an outlet 2 to a humidification chamber 3 which is heated by the heater plate 4 of a respiratory humidifier 5. Water within humidification chamber 3 is heated, producing water vapour which humidifies the gases within the chamber which are then passed out through outlet 6 into a heated gases transportation pathway or inspiratory respiratory conduit 7. A conventional "Y-piece" 8 receives gases from conduit 7 and allows the gases to pass to a patient through an outlet 9. Gases exhaled by the patient are then passed back through "Y-piece" 8 into a further heated gases transportation pathway or expiratory conduit 10 and back to ventilator 1.

The humidifier 5 is provided with a controller 11, such as a micro-processor, which receives inputs from user adjustable dials (such as temperature setting dial 12) and from temperature sensors (such as sensors 13 and 14 and may also include an ambient temperature sensor 15) and appropriately controls the energisation of heater plate 4 in accordance with a control system or set of instructions, such as a software program, to provide humidified gases to the patient at a desired temperature and/or relative humidity. It will be appreciated that gases leaving outlet 6 of humidification chamber 3 will have a relative humidity of around 100% and that as the gases travel along conduit 7 there is a chance that water vapour may condense on the conduit wall, detrimentally reducing the water content of the gases. It is preferable that the water content of the humidified gases supplied to the patient is as high as possible.

In order to minimise the occurrence of condensation within conduit 7 and also within conduit 10, a heater wire may be provided within each of the conduits. The heater wire is preferably an insulated "Nichrome" (nickel/chromium alloy) resistance wire wound around an insulating core. The resistance per unit length of the heater wire is much less than in the prior art, however the total resistance is comparable to prior art heater wires as the present invention utilises a greater length of wire within the conduit. Power is supplied to the heater wires from the humidifier 5 via connections 16 and 17 which plug into sockets in cuffs at an end of each conduit. Preferably the insulating coating around the heater wire is a thermoplastics material which, when heated to a predetermined temperature, enters a state in which its shape may be altered and the new shape substantially elastically retained upon cooling.

With reference to FIGS. 1 to 4, a section of the preferred form of conduit 7 (or 10) is shown in detail. The conduit is for example moulded from an elastomeric material such as a Polyethylene/EVA mixture or silicon rubber. The conduit preferably has a "ribbed" or "corrugated" construction to allow bending (the ribs are referenced 21) and this may be accomplished by blowing the molten elastomeric material to form an endless cylinder which is forced outwards against the internal surface of a rotating mould which impresses the ribs onto the conduit. Within conduit 7 (or 10), a helically wound heater wire 20. The heater wire 20 preferably sits against or adjacent to the internal wall of the conduit along its length as can be seen in FIG. 2, or alternatively the heater wire may be of a diameter less than the internal diameter of the conduit in which case the helically wound wire will distribute itself within the conduit.

In order to shape the heater wire 20 into its preferred helical form it is first wound (preferably tight) around a former into a helix prior to insertion within the conduit. The heater wire 20, while wound on its former, is then heated to a predetermined temperature which will soften the insulating coating of the wire such that, upon cooling, the heater wire will retain its new, helical shape. The aforementioned heating may be accomplished by placing the wound wire and former within an oven for a predetermined length of time which has been heated to a suitable temperature or alternatively, the ends of the spirally wound wire may be connected to a power supply and a voltage applied such that a greater than rated current is caused to flow through the wire for a predetermined length of time. The voltage and duration would be selected so as to achieve the desired result of softening (but not melting) the insulating coating. The former could be a tube or cylinder with an outside diameter smaller than the internal diameter of the conduit 7.

The pitch of the heater wire helix may be adjusted during the winding stage so that the completed heated conduit may be tailored to suit the ambient conditions that the particular humidification system will be operated under. That is, if the ambient temperature is likely to be very cold, then the pitch of the helix may be wound tighter (adjacent turns closer together) such that when energised, the mid point on the conduit wall between two adjacent turns does not drop to a temperature at which condensation would be likely to occur. Conversely, if the temperature were likely to be rather warm, then the pitch could be increased whereby the overall length of wire within the conduit could be decreased, decreasing production costs. It will be understood that a helically wound heater wire effectively circumscribes a cylindrical volume of gases, allowing the humidified gases to freely flow through the conduit substantially without introducing impedance to the flow while offering a large effective surface area of the heater wire to the gases flow, improving heat transfer.

It should be noted that there is a trade-off between the amount of condensation occurring in a conduit (more wire reduces condensation), the amount of heat supplied by the heater wire (more wire increases heat supplied) and the resistance to flow offered by the heater wire (more wire increases the flow resistance). By experiment we have found that a helical pitch of between about 1 and about 20 turns per 50 mm of conduit and a helix diameter of between about 8 and about 20 mm produce a heater wire which has good heating characteristics and is a good compromise between the aforementioned conflicting requirements.

Once the heater wire helix has been formed, the former and attached heater wire may be inserted into the conduit, or alternatively, the helix could first be removed from the former. Once inside the conduit, the former is removed and the inherent elastic property of the heater wire will tend to cause an enlargement in the diameter of the helix, thus tending to force the heater wire helix against the internal wall of the conduit. Alternatively, as has already been mentioned the heater wire helix may be of a diameter less than the inner diameter of the conduit in which case the heater wire helix would lie to one side of the conduit inner wall. One end of the heater wire is then terminated in a socket 18 or 19 which is seated in a cuff at an end of the conduit while the other end of the heater wire is connected at the other end of the conduit to a return current path which may comprise a low resistance "earth" wire along the outside of the conduit. When a low resistance wire is included as a return, the voltage at the connection point would be substantially zero volts which is advantageous in some medical environments where sensitive monitoring equipment is positioned in the vicinity of the connection point (near the patient's head). Alternatively in a more preferred embodiment shown in FIG. 12, the heater wire could be wound as a double helix so that both ends of the heater wire are provided at one end of the conduit (or a double helix could be formed from a heater wire connected at one end to a low resistance return wire). The free end of the return wire is also terminated in socket 18 or 19 in the conduit cuff. Electrical connectors 16 and 17 are plugged into sockets 18 and 19 respectively in order to provide the heater wires in the conduits with current under control of controller 11 so that, in response to temperature readings, the heater wires may be controllably energised to reduce condensation occurring within the conduit.

Figure 12:
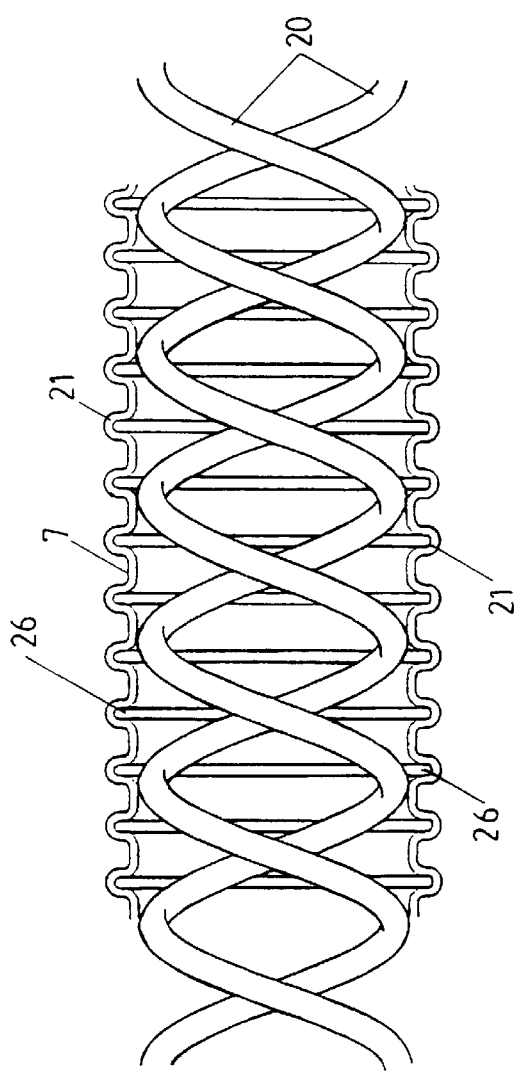
FIG. 12 is a sectional view of a section of a heated respiratory conduit in accordance with a second preferred embodiment of the present invention showing the heater wire wound in a double helix.

In the case of a double helically wound heater wire (as shown in FIG. 12), if the heater wire were held only at one end of the conduit (the end of the conduit where the heater wire ends are terminated in sockets 18 or 19) then the heater wire would tend to elastically return to its tightly wound state, extending only a fraction of the way along the conduit. In order to avoid this problem the end of the double helix furthest from the terminated ends of the wires should be held in place at or near the end of the conduit furthest from sockets 18 and 19. This may be accomplished in a number of known ways such as by attaching a circular clip (not shown) to the heater wire near its "doubled over" end then fixing the clip to the inside of the conduit. Preferably the circular clip is a good fit within one of the internal cylindrical grooves 26 of the conduit (the clip within the cylindrical groove may be compared to an inner tube sitting within a tire). The positioning of the clip within the end of the conduit may also be used to control the pitch of the helically wound wire to overcome condensation which may occur between adjacent turns of the wire.

It has been found that a heated helically wound humidifier conduit, constructed according to the present invention, has the benefit of improved energy transfer from the heater wire to the gases flow within the conduit. This is due to the fact that the gases flow passes across most of the wire's surface along the wire's entire length (which is much greater than the length of the conduit) and also due to the fact that the heater wire interacts with the gases flow across the width of the conduit. Accordingly, the gases flow around the entire circumference of the conduit will be warmed by the heater wire. This fact is displayed graphically in FIG. 6 where only a single helix is illustrated and where it can be seen that the temperature distribution across the width of the conduit, due to the arrangement of the heater wire, is more even than the distribution which is encountered in prior art systems where a heater wire lies longitudinally within the conduit (see FIG. 5). A double helix provides an even better heating performance over the single helix while also allowing both ends to be terminated in a single cuff without the need for a return wire. It can be seen in FIG. 5 that the temperature in the prior art conduit is highest close to the wire but the temperature of the conduit wall across from the heater wire drops significantly, so that condensation may be likely to occur at this point and the gases within the conduit will not be uniformly warmed.

Accordingly, due to the improved efficiency in the transfer of energy to the gases, the temperature of the heater wire may be reduced when compared to the prior art reducing the risk of melting the conduit. Prior heated conduits wherein heater wires were wound around the outside of the conduit were required to transmit energy through the conduit in order to heat the gases. The present invention improves the energy efficiency (as the humidified gases are heated evenly both across and along the conduit) and thus the overall energy requirement of the humidification system reducing the power drawn by the heater wire (even if the total resistance of the heater wire will ordinarily be substantially equivalent to the prior art).

Figure 7:
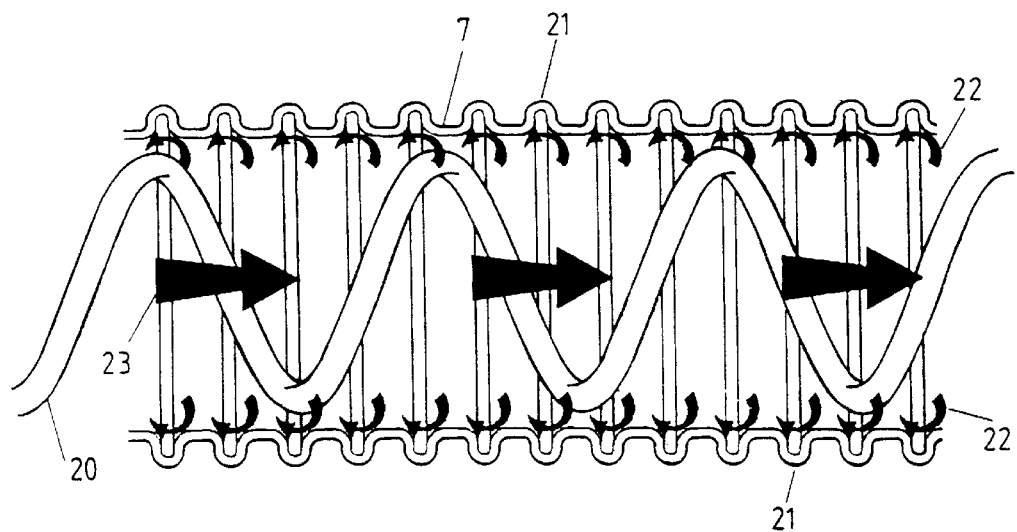
FIG. 7 is an enlarged view of a section of the conduit shown in FIG. 3.
Figure 8:
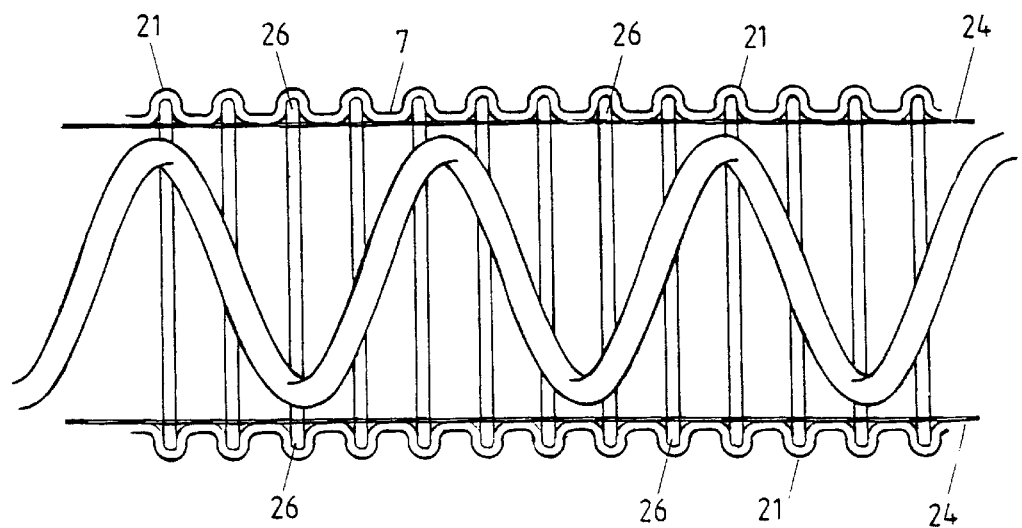
FIG. 8 is an enlarged sectional view of the conduit of FIG. 3 with an internal sheath between the conduit inner wall and the helically wound heater wire.
Figure 9:
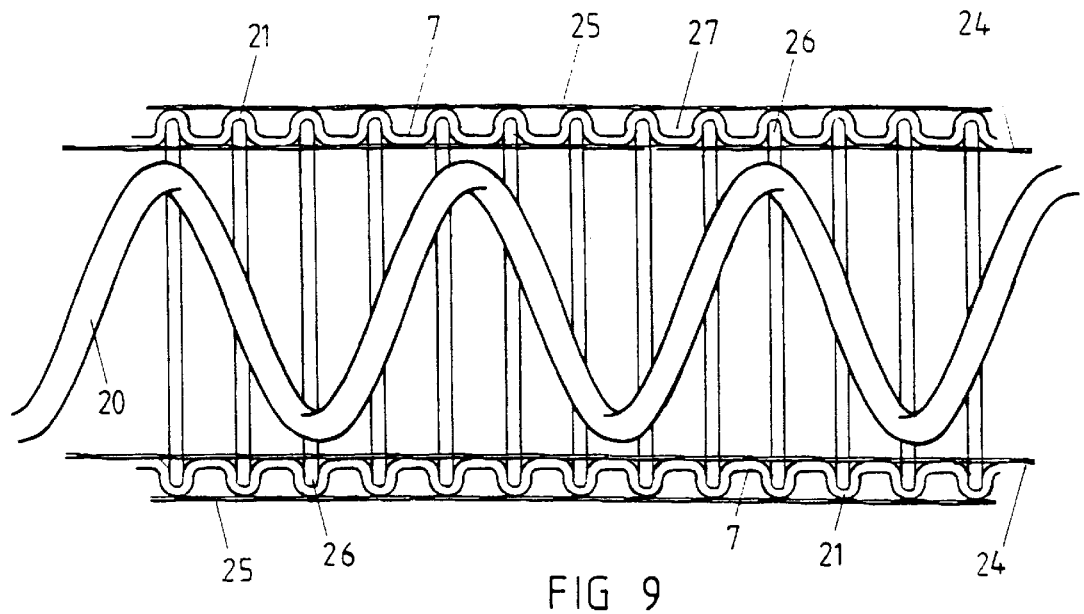
FIG. 9 is an enlarged sectional view of the conduit of FIG. 8 with an external sheath around the conduit.
Figure 10:
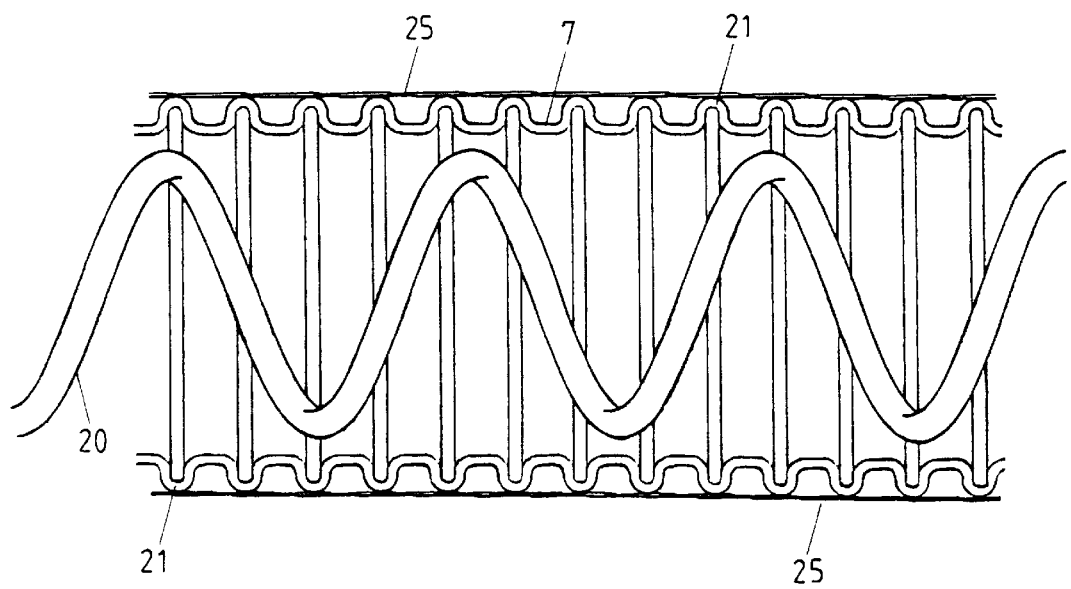
FIG. 10 is an enlarged sectional view of the conduit of FIG. 3 with an external sheath around the conduit.

With reference to FIG. 7, it can be seen that gases flow 23 within a ribbed or corrugated conduit produces small eddies 22 within the depressions in the internal conduit wall. This phenomenon detrimentally increases the transfer of heat energy from the gases to the conduit wall and out to the ambient surroundings as the heated gases in the eddies continually circulate passing heat to the conduit wall on each pass. In an effort to reduce this problem and to further improve energy efficiency, an inner sheath 24 of, for example, thin plastics material may be inserted within the conduit in the space between the helix formed by the heater wire 20 and the inner conduit wall. This step could be carried out prior to inserting the wire into the conduit, or alternatively, the inner sheath could be extruded along with the conduit. The ends of the sheath are then bonded or sealed to the conduit. The gases supply from the humidifier chamber is then forced to flow solely through inner sheath 24 and across the heater wire, an insulating layer of stagnant air 26 formed between inner sheath 24 and conduit 7 further reducing heat transfer to the surroundings and reducing the effect of changes in ambient temperature on the temperature of the gases and eliminating eddies while maintaining the suppleness of the ribbed conduit. To still further improve the energy efficiency of the heated conduit the entire conduit/heater wire/inner sheath construction may be inserted into an outer sheath 25 as shown in FIG. 9 with the ends bonded or otherwise sealed to the conduit ends. A further layer of stagnant air 27 is thus added to the conduit "sandwich" to reduce energy transfer to the surroundings. If the diameter of the outer sheath is a tight fit around the conduit then a series of insulating cylindrical stagnant air pockets will be formed between the conduit and the outer sheath rather than a continuous cylinder, further insulating the conduit from changes in ambient conditions. Alternatively, as shown in FIG. 10, an outer sheath could be used without the necessity of also adding an inner sheath.

Figure 13:
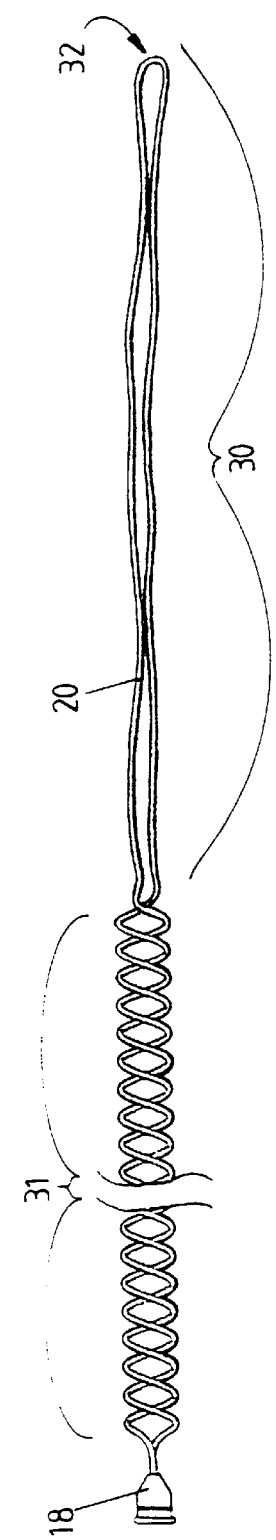
FIG. 13 is a front elevation of the heater wire of FIG. 12 with an additional optional straight loop section.

With reference to FIG. 13 a further optional feature of the heater wire according to the present invention is shown. In this embodiment the heater wire is wound so as to possess two distinct sections, a double helically wound section 31 and a simple loop section 30. In order to ensure that the heater wire is evenly distributed along the conduit, a clip (not shown) may be used to fix end 32 of the heater wire at or near the end of the conduit (as has been described previously) or a clip could hold the heater wire at the point between the helically wound section 31 and the simple looped section 30. The benefit of incorporating simple loop section 30 can be explained with reference to the respiratory humidification set up shown in FIG. 14.

Figure 14:
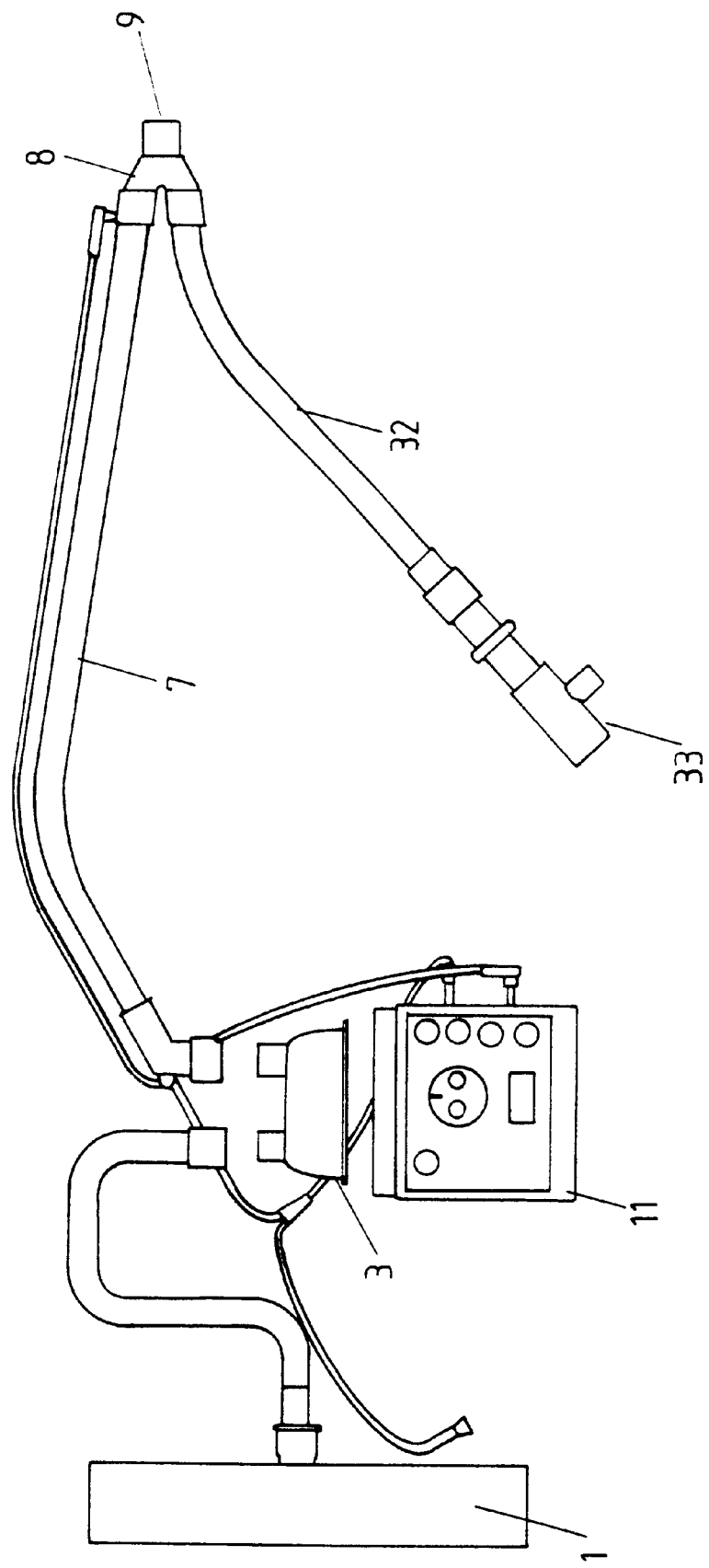
FIG. 14 is a partially exploded view of an alternative preferred respiratory humidification system especially suited for use as an intubated CPAP setup which, when used in conjunction with the heater wire of FIG. 13, may easily be converted to the humidification system of FIG. 11.

FIG. 14 shows how a humidification system may be set up for "Intubated CPAP" (Continuous Positive Airway Pressure). This configuration is the same as that shown in FIG. 11 except that the expiratory conduit 10 in FIG. 11 has been replaced with a shorter conduit 32 which has a CPAP valve 33 connected at its free end for generating a constant pressure at the patient. The expiratory conduit 10 in FIG. 11 may be made up of two connected conduits 32 and another (not shown). The heater wire of FIG. 13 may then be inserted into the expiratory limb of the breathing circuit (section 30 being positioned within conduit 32 and section 31 being positioned within the second short conduit (not shown)). Then, in order to produce the configuration of FIG. 14, the second short conduit and heater wire 20 need only be removed and the CPAP valve 33 added. The benefit of straight section 32 is evident when reconfiguring the system of FIG. 14 to reproduce the system of FIG. 11. In this reconfiguration, because simple loop section 30 of heater wire will be protruding from the second short conduit, it can easily be fed back into conduit 32 whereas a helical conduit could not easily be inserted by the user.

Figure 15:
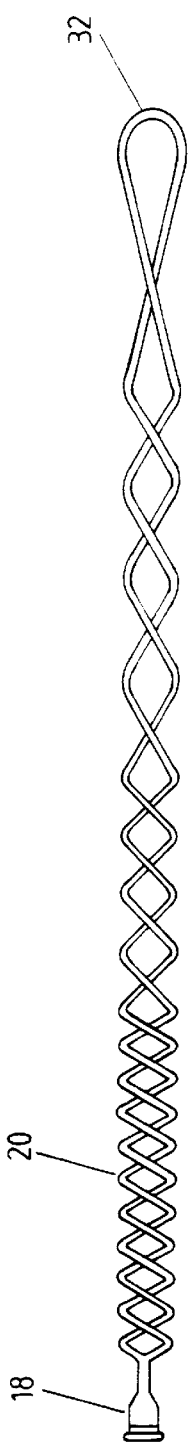
FIG. 15 is a front elevation of an alternative wound heater wire configuration to that shown in FIG. 12.

A still further alternative preferred embodiment of wound heater wire configuration is shown in FIG. 15. The wound heater wire of FIG. 15 is produced from the same insulated resistance wire of the previous preferred embodiments and may be used with or without the addition of inner/outer sheaths (it is anticipated that inner/outer sheaths will not be necessary with this embodiment). It can be seen that the heater wire has been wound into a double helix with a variable pitch along the wire. Preferably the pitch is smallest at one end and increases towards the other. However a different varying pitch configuration than that shown may be preferable depending on the circumstances of use.

One benefit of the pitch configuration shown in FIG. 15 is that the wound wire may be inserted into a conduit such that the tightly wound end (smallest pitch) may be positioned at the end of the respiratory conduit 7 closest to humidifier 5. As the humidified gases leave outlet 6 at their greatest level of relative humidity, condensation is ordinarily more likely to occur so a greater amount of heating should be provided at this position. Thus, the tightly wound end of the heater wire 20 provides an increased level of heating at the position in the conduit where it is required. It has been found that the variable pitch double helically wound heater wire of FIG. 15 produces a reduction in condensation, especially at the humidifier outlet while also maintaining the gases temperature along the entire conduit.

Figure 16:
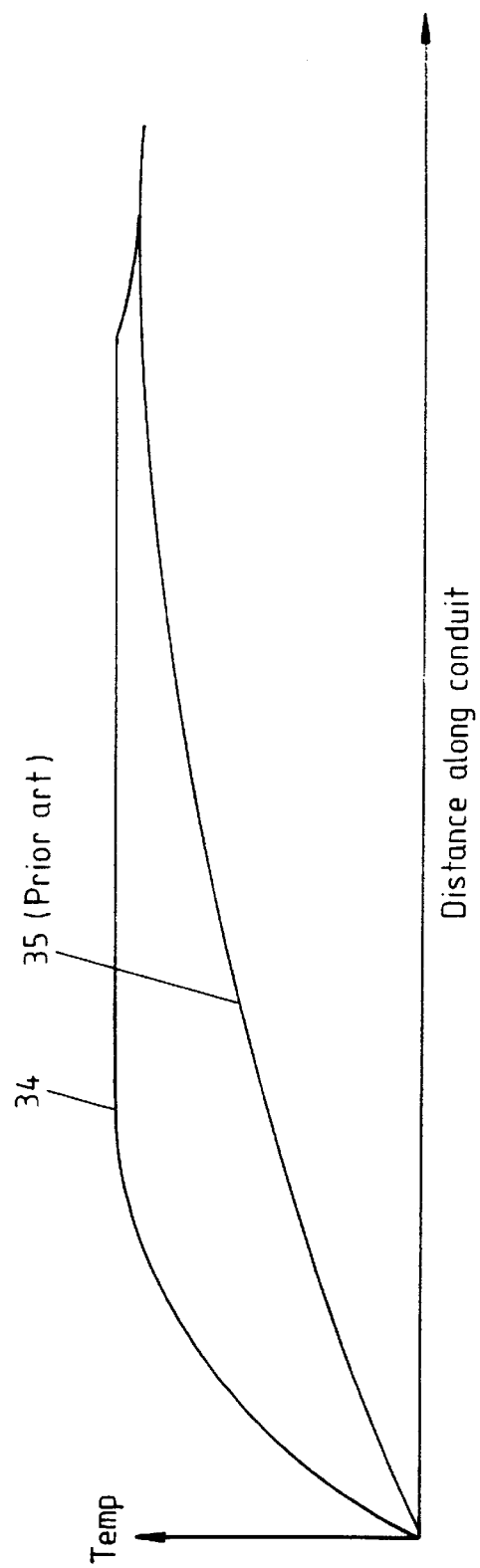
FIG. 16 is a graph of temperature versus distance along the conduit showing a comparison between a conventional prior art heater wire and the heater wire of FIG. 15.

A similarly wound heater wire could be used in the expiratory conduit 10, however the tightly wound end should be positioned at the end of the conduit closest to the patient's head, as this is where the expired gases will have their greatest level of relative humidity and thus this is the area having the greatest risk of condensation occurring. The benefit of this heater wire configuration is demonstrated in FIG. 16 where it can be seen that the temperature of gases near the end of the conduit connected to the humidifier is near maximum with the heater wire constructed according to the present invention (line 34) compared to the prior art heated conduits (line 35) in which temperature gradually increases along the conduit to a maximum near the end.

Preferably the pitch of the heater wire lies in the range of between about 1 (smaller pitch) to about 20 (larger pitch) turns per 50 mm of conduit when the wire is installed in the conduit.

In order to produce the variable pitch double helically wound heater wire of FIG. 15 a similar process is carried out as that described with reference to the previous embodiments. Preferably the resistance wire is tightly wound onto a rotating former, first in one direction on the former to form a first layer and then back the other way on top of the previous layer to the start position. In this embodiment however, in order to form a variable pitch, the former is a tapered rod (or frusto-conical shaped rod). In order to produce the heater wire shown in FIG. 15, the tapered rod preferably has a small end diameter of about 3 mm and a large end diameter of about 18 mm. After winding and heating (as previously described) the wire is removed from its former and allowed to elastically assume its new form having a diameter from about 4 mm to about 20 mm. Upon stretching longitudinally the wound heater wire may, depending on the properties of the thermoplastics coating and the shape of the former used, conform to a substantially constant diameter along its length with the required variable pitch. Alternatively, the stretched, formed wire may conform to a variable pitch and/or variable diameter heater wire. The tight pitch/small diameter region of stretched heater wire is formed from the narrow end of the tapered forming rod while the larger pitch/larger diameter region is formed from the large end of the former rod. The reason for this can be better understood with the use of an analogy to a spring where tightly wound springs (small pitch) do not stretch as easily as springs which are wound less tightly (large pitch). The ends of the wound variable pitch heater wire may then be terminated in sockets 18 or 19 for connection in the conduit end cuffs, while the opposite "doubled over" end of the helically wound wire may be held in place within the conduit by, for example, a circular clip as has been previously described.

Thus, at least in the preferred form, the present invention provides a heated humidifier conduit in which the gases and the conduit are more evenly heated, reducing the risk that condensation will occur. The present invention also allows for more even heat distribution of the gases within the conduit due to the fact that a length of heater wire which is much greater than the length of the conduit, is distributed within the conduit at the positions both across and along the conduit which most advantageously reduce condensation. The construction also improves the overall energy efficiency of a respiratory humidification system and reduces the effect on gases temperature of changes in ambient conditions.

What is claimed is:

1. A heated gases transportation pathway for use in a ventilation system adapted to supply a gases flow to said gases transportation pathway comprising:

a conduit means of a predetermined length adapted to channel said gases flow, a heating means of a predetermined length adapted to heat said gases flow and/or said conduit means wherein said heating means is positioned within said conduit means and in said gases flow wherein said heating means are helically wound and wherein the pitch and/or diameter of said helix varies along the length of said conduit means in order that said heating means may provide variable levels of heat at different positions within said conduit means.

2. A heated gases transportation pathway for use in a ventilation system including a humidifier and adapted to supply a gases flow to said gases transportation pathway, comprising:

an inspiratory conduit of a predetermined length adapted to supply said gases to a patient from a humidifier end of said inspiratory conduit to a patient end of said inspiratory conduit, a heating means of a predetermined length formed from a length of insulated resistance wire wound into a double helix with both ends of said wire provided at one end of said conduit adapted to heat said gases flow and/or said conduit wherein said heating means is positioned within said conduit and in said gases flow wherein the pitch and/or diameter of said helix varies along the length of said conduit in order that said heating means may provide variable levels of heat at different positions within said conduit and wherein the pitch of said helically wound resistance wire is tighter at said humidifier end.

3. A heated gases transportation pathway for use in a ventilation system adapted to supply a gases flow to said gases transportation pathway comprising:

a conduit means of a predetermined length, a heating means of a predetermined length adapted to heat said gases flow and/or said conduit means wherein said heating means is positioned within said conduit means and in said gases flow wherein said heating means are helically wound and wherein the pitch and/or diameter of said helix varies along the length of said conduit means in order that said heating means may provide variable levels of heat at different positions within said conduit means, and wherein said heating means is elastically flexible and has an electrically insulating thermoplastics coating which assists said heating means in retaining shape wherein when wound into a new shape and heated above a predetermined temperature, said heating means will, upon cooling, tend to elastically retain said new shape.

4. A heated gases transportation pathway for use in a ventilation system adapted to supply a gases flow to said gases transportation pathway comprising:

a conduit means of a predetermined length adapted to channel said gases flow, a heating means of a predetermined length adapted to heat said gases flow and/or said conduit means wherein said heating means is positioned within said conduit means and in said gases flow wherein said heating means are helically wound and wherein the pitch and/or diameter of said helix varies along the length of said conduit means in order that said heating means may provide variable levels of heat at different positions within said conduit means, and wherein parts of said heating means are adjustably fixed to said conduit in order to adjustably fix the pitch and/or diameter of said helically wound wire, the pitch and/or diameter requiring adjustment in order to minimize condensation occurring between adjacent turns of said helically wound wire.

5. A heated gases transportation pathway as claimed in claim 1 or claim 2 wherein said conduit means is an expiratory conduit adapted to channel said gases from a patient at a patient end of said expiratory conduit means to a discharge end of said expiratory conduit means, wherein the pitch of said helix is tighter at said patient end.

6. A heated gases transportation pathway as claimed in claim 1 or claim 2 wherein the pitch of said helix varies between about 1 to about 20 turns per 50 mm of conduit.

7. A heated gases transportation pathway as claimed in claim 1 or claim 2 wherein the diameter of said helically wound resistance wire is between about 8 mm and about 20 mm.

8. A heated gases transportation pathway as claimed in claim 1 or claim 2 wherein an inner sheath is inserted within and co-axial with said conduit means, the ends of said inner sheath being sealed to said conduit means such that an insulating layer of trapped gases is formed between said inner sheath and said conduit means with said heating means provided within said inner sheath.

9. A heated gases transportation pathway for use in a ventilation system adapted to supply a gases flow to said gases transportation pathway comprising:

a conduit means of a predetermined length adapted to channel said gases flow, a heating means of a predetermined length adapted to heat said gases flow and/or said conduit means wherein said heating means is positioned within said conduit means and in said gases flow wherein said heating means are helically wound and wherein the pitch and/or diameter of said helix varies along the length of said conduit means in order that said heating means may provide variable levels of heat at different positions within said conduit means, and wherein said heating means comprises a length of electrically insulated resistance wire having two sections, a first double helically wound section and a second simple loop section, said double helically wound section including the two ends of said resistance wire and said simple loop section being furthest from the two ends of said resistance wire.

10. A heated gases transportation pathway as claimed in claim 9 wherein the pitch of said helically wound resistance wire is between about 1 to about 20 turns per 50 mm of conduit.

11. A heated gases transportation pathway for use in a ventilation system which creates a gases flow comprising:

a conduit means adapted to channel said gases flow, a heating means adapted to, upon energisation, supply heat to said gases flow within said conduit means, wherein said heating means is provided in said gases flow within said conduit means and is formed from a single length of insulated resistance wire wound into a helix and wherein said resistance wire is insulated with a layer of thermoplastics material so that said wire may be wound into said helix, heated and then cooled to cause said wire to tend to elastically retain said helical shape.

12. A heated gases transportation pathway as claimed in claim 11 wherein the pitch of said helix varies along said heating means.

13. A heated gases transportation pathway as claimed in claim 11 wherein said insulated resistance wire extends substantially between both ends of said conduit means with a return current path supplied by a low resistance return wire connected to one end of said insulated resistance wire which also extends substantially between both ends of said conduit means.

14. A heated gases transportation pathway for use in a ventilation system which creates a gases flow comprising:

a conduit means adapted to channel said gases flow, a heating means adapted to, upon energization, supply heat to said gases flow within said conduit means, wherein said heating means is provided in said gases flow within said conduit means and is formed from a single length of insulated resistance wire wound into a helix and wherein said resistance wire is insulated with a layer of thermoplastics material so that said wire may be wound into said helix, heated and then cooled to cause said wire to tend to elastically retain said helical shape, and wherein said conduit means comprises a corrugated tube, an inner sheath co-axial with said conduit means is provided between the heating means and the inner surface of said conduit means forming a series of insulating spaces between the corrugations of said conduit means and said inner sheath.

15. A heated gases transportation pathway as claimed in claim 11 wherein said conduit means comprises a corrugated tube, an outer sheath is provided external to and co-axial with said conduit means in order to form an outer insulating space around said conduit means and wherein said sheath is a substantially tight fit about said conduit means such that said outer insulating space comprises a series of insulating spaces between said corrugations of said conduit means and said outer sheath.

16. A heated gases transportation pathway for use in a ventilation system which creates a gases flow comprising:
a conduit means adapted to channel said gases flow,
a heating means adapted to, upon energization, supply heat to said gases flow within said conduit means, wherein said heating means is provided in said gases flow within said conduit means and is formed from a single length of insulated resistance wire wound into a helix and wherein said resistance wire is insulated with a layer of thermoplastics material so that said wire may be wound into said helix, heated and then cooled to cause said wire to tend to elastically retain said helical shape, and
wherein the pitch and/or diameter of said helically wound insulated resistance wire is adjustable by adjustably fixing a part of said resistance wire to said conduit means such that adjustment of said pitch and/or diameter may be made by adjusting the position of fixing in order that condensation may be substantially eliminated from the spaces between adjacent turns of said wire on the inner wall of said conduit means.

17. A heated gases transportation pathway as claimed in claim 11 wherein the pitch of said helically wound insulated resistance wire is between about 1 to about 20 turns per 50 mm of conduit.

18. A heated gases transportation pathway as claimed in claim 11 wherein the diameter of said helically wound insulated resistance wire is between about 8 and about 20 mm.

19. A heated gases transportation pathway as claimed in claim 11 wherein said conduit means comprise an inspiratory conduit adapted to supply said gases to a patient from a humidifier end of said inspiratory conduit to a patient end of said inspiratory conduit, wherein the pitch of said helix is tighter at said humidifier end.

20. A heated gases transportation pathway as claimed in claim 11 wherein said conduit means comprise an expiratory conduit adapted to channel said gases from a patient at a patient end of said expiratory conduct to a discharge end of said expiratory conduit, wherein the pitch of said helix is tighter at said patient end.

21. A method of producing a heated gases transportation pathway for use in a ventilation system comprising the steps of:
i) forming a conduit through which gases may be channelled,
ii) winding a predetermined length of thermoplastically insulated resistance wire into a helix of a diameter less than the inside diameter of said conduit,
iii) heating the helically wound resistance wire to a predetermined temperature at which said insulation is softened,
iv) cooling said heated resistance wire so that the cooled resistance wire will tend to elastically retain its helically wound shape, and
v) inserting the thus formed helically wound resistance wire into said conduit.

22. A method of producing a heated gases transportation pathway as claimed in claim 21 wherein said step of winding includes ensuring that the pitch of said helix is varied along the length of the conduit.

23. A method of producing a heated gases transportation pathway as claimed in claim 21 or claim 22 wherein said step of heating is carried out by connecting the ends of the helically wound heater wire to a source of voltage and causing a current to flow through said resistance wire of a sufficient magnitude for a predetermined time to raise the temperature of said insulating coating above said predetermined temperature.

24. A method of producing a heated gases transportation pathway as claimed in claim 21 or claim 22 wherein said step of heating is carried out by placing the helically wound heater wire in a heating means until said insulating coating has reached said predetermined temperature for a predetermined time.

25. A method of producing a heated gases transportation pathway as claimed in claim 21 or claim 22 wherein said step of winding said resistance wire includes ensuring that the diameter of said helically wound resistance wire is between about 8 mm and about 20 mm.

26. A method of producing a heated cases transportation pathway as claimed in claim 21 or claim 22 wherein said step of winding said resistance wire includes ensuring that the pitch of said resistance wire is between about 1 and about 20 turns per 50 mm of conduit.

27. A method of producing a heated gases transportation pathway as claimed in claim 21 or claim 22 wherein said method also includes the step of inserting an inner sheath, within and co-axial with said conduit, prior to said step of inserting said helically wound resistance wire into said conduit and sealing the ends of said sheath to said conduit such that an insulating layer of trapped gases are formed between said inner sheath and said conduit.

28. A method of producing a heated gases transportation pathway as claimed in claim 21 or claim 22 wherein said step of winding includes the step of connecting a low resistance return wire to one end of said helically wound wire, the two remaining ends of the heater wire and low resistance wire combination being provided at one common end of said conduit.

29. A method of producing a heated gases transportation pathway as claimed in claim 21 or claim 22 wherein said step of winding is carried out on a substantially cylindrical former by winding a first layer of wire upon said former in a first direction along said former and then reversing direction along said former and forming a second layer on top of said first layer such that the wound wire will have a substantially constant pitch when stretched.

30. A method of producing a heated gases transportation pathway as claimed in claim 21 or claim 22 wherein the step of winding is carried out on a substantially frusto-conical or tapered former by winding a first layer of wire upon said former in a first direction along said former and then reversing direction along said former and forming a second layer on top of said first layer such that the wound wire will have a variable pitch and/or diameter when stretched.

31. A method of producing a heated gases transportation pathway as claimed in claim 21 or claim 22 wherein the pitch of said wound wire varies between about 1 and about 20 turns per 50 mm of conduit.

32. A method of producing a heated gases transportation pathway as claimed in claim 21 or claim 22 wherein said conduit comprises an inspiratory conduit adapted to supply said cases to a patient from a humidifier end of said inspiratory conduit to a patient end of said inspiratory conduit, wherein said step of inserting the helically wound resistance wire into said conduit includes the step of arranging that the pitch and/or diameter of said helically wound wire is tightest at said humidifier end of said inspiratory conduit.

33. A method of producing a heated gases transportation pathway as claimed in claim 21 or claim 22 wherein said conduit comprises an expiratory conduit adapted to channel said gases from a patient at a patient end of said expiratory conduit to a discharge end of said expiratory conduit, wherein said step of inserting the helically wound resistance wire into said conduit includes the step of arranging that the pitch and/or diameter of said helically wound wire is tightest at said patient end of said expiratory conduit.

34. A heated gases transportation pathway for use in a ventilation system including a humidifier and adapted to supply a gases flow to said gases transportation pathway, comprising:

an inspiratory conduit of a predetermined length adapted to supply said gases to a patient from a humidifier end of said inspiratory conduit to a patient end of said inspiratory conduit, a heating means of a predetermined length formed from a length of insulated resistance wire wound into a double helix with both ends of said wire provided at one end of said conduit adapted to heat said gases flow and/or said conduit wherein said heating means is positioned within said conduit and in said gases flow wherein the pitch and/or diameter of said helix varies along the length of said conduit in order that said heating means may provide variable levels of heat at different positions within said conduit and wherein the pitch of said helically wound resistance wire is tighter at said humidifier end, and wherein said heating means is elastically flexible and has an electrically insulating thermoplastics coating which assists said heating means in retaining shape wherein when wound into a new shape and heated above a predetermined temperature, said heating means will, upon cooling, tend to elastically retain said new shape.

* * * * *

UNITED STATES PATENT AND TRADEMARK OFFICE
CERTIFICATE OF CORRECTION

PATENT NO. : 6,078,730
DATED : June 20, 2000
INVENTOR(S) : Brett J. Huddart and Malcolm H. Cambridge It is certified that error appears in the above-identified patent and that said Letters Patent is hereby corrected as shown below:

Column 11, Line 51 "conduct" should be -- conduit --

Column 12, Line 26 "cases" should be -- gases --

Column 13, Line 2 "cases" should be -- gases --

Signed and Sealed this

Third Day of April, 2001

*Attest:*

NICHOLAS P. GODICI

*Attesting Officer*   *Acting Director of the United States Patent and Trademark Office*